United States Patent
Wilmer et al.

(10) Patent No.: US 8,492,566 B2
(45) Date of Patent: Jul. 23, 2013

(54) METHOD FOR STARTING A GAS-PHASE OXIDATION REACTOR

(75) Inventors: Hagen Wilmer, Ludwigshafen (DE); Jürgen Zühlke, Speyer (DE); Thomas Lautensack, Birkenau (DE); Hans-Martin Allmann, Neunkirchen (DE); Frank Rosowski, Mannheim (DE); Cornelia Katharina Dobner, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 315 days.

(21) Appl. No.: 12/936,807

(22) PCT Filed: Apr. 7, 2009

(86) PCT No.: PCT/EP2009/054168
§ 371 (c)(1),
(2), (4) Date: Oct. 7, 2010

(87) PCT Pub. No.: WO2009/124946
PCT Pub. Date: Oct. 15, 2009

(65) Prior Publication Data
US 2011/0034707 A1 Feb. 10, 2011

(30) Foreign Application Priority Data
Apr. 7, 2008 (EP) .................................... 08154169

(51) Int. Cl.
*C07D 307/89* (2006.01)
(52) U.S. Cl.
USPC ........................................................ 549/248

(58) Field of Classification Search
USPC ........................................................ 549/248
See application file for complete search history.

(56) References Cited

U.S. PATENT DOCUMENTS

| 4,077,984 A | 3/1978 | Blechschmitt et al. |
| 4,284,571 A | 8/1981 | Sato et al. |

(Continued)

FOREIGN PATENT DOCUMENTS

| DE | 2005969 A1 | 8/1971 |
| DE | 2546268 A1 | 4/1977 |

(Continued)

OTHER PUBLICATIONS

U.S. Appl. No. 13/052,140, Altwasser et al.

(Continued)

*Primary Examiner* — Taylor Victor Oh
(74) *Attorney, Agent, or Firm* — Novak Druce Connolly Bove + Quigg LLP

(57) ABSTRACT

What is described is a process for starting up a gas phase oxidation reactor for oxidation of o-xylene to phthalic anhydride, said reactor comprising at least one catalyst layer and being temperature-controllable by means of a heat carrier medium, wherein a) the catalyst layer is interrupted by a moderator layer which is less catalytically active than the catalyst layer or is catalytically inactive, b) a gas stream is passed through the reactor with an initial loading of o-xylene and at an initial temperature of the heat transfer medium, c) the loading of the gas stream is increased to a target loading and, in parallel, the temperature of the heat transfer medium is lowered to an operating temperature. The introduction of the moderator layer allows the loading to be increased more rapidly and the startup time to be shortened.

9 Claims, 3 Drawing Sheets

U.S. PATENT DOCUMENTS

| | | | |
|---|---|---|---|
| 4,481,304 A | 11/1984 | Sato et al. | |
| 5,969,160 A | 10/1999 | Lindstrom | |
| 6,700,000 B1 | 3/2004 | Heidemann et al. | |
| 8,067,618 B2 * | 11/2011 | Lautensack et al. | 549/248 |
| 2007/0270597 A1 | 11/2007 | Wilmer et al. | |
| 2008/0177105 A1 | 7/2008 | Raichle et al. | |
| 2008/0214863 A1 | 9/2008 | Cremer et al. | |
| 2008/0307648 A1 | 12/2008 | Cremer et al. | |
| 2008/0312477 A1 | 12/2008 | Raichle et al. | |
| 2009/0118531 A1 | 5/2009 | Hibst et al. | |
| 2009/0156835 A1 | 6/2009 | Mackewitz et al. | |
| 2009/0163726 A1 | 6/2009 | Wilmer et al. | |
| 2009/0171101 A1 | 7/2009 | Lautensack et al. | |
| 2009/0198073 A1 | 8/2009 | Mackewitz et al. | |
| 2009/0270640 A1 | 10/2009 | Maurer et al. | |
| 2009/0286999 A1 | 11/2009 | Wilmer et al. | |
| 2009/0318712 A1 | 12/2009 | Wilmer et al. | |
| 2010/0029955 A1 | 2/2010 | Wilmer et al. | |
| 2010/0069659 A1 | 3/2010 | Raichle et al. | |
| 2010/0069660 A1 | 3/2010 | Raichle et al. | |
| 2011/0028740 A1 | 2/2011 | Dobner et al. | |
| 2011/0118487 A1 | 5/2011 | Abdallah et al. | |
| 2011/0124885 A1 | 5/2011 | Altwasser et al. | |

FOREIGN PATENT DOCUMENTS

| | | |
|---|---|---|
| DE | 2948163 A1 | 6/1980 |
| DE | 19807018 A1 | 8/1998 |
| DE | 19823262 A1 | 12/1999 |
| EP | 163231 A1 | 12/1985 |
| EP | 286448 A2 | 10/1988 |
| EP | 1852413 A1 | 11/2007 |
| WO | WO-98/00778 A1 | 1/1998 |
| WO | WO-2005/063673 A1 | 7/2005 |
| WO | WO-2008/022909 | 2/2008 |
| WO | WO-2008/022909 A1 | 2/2008 |
| WO | WO-2008/022911 | 2/2008 |
| WO | WO-2008/022911 A1 | 2/2008 |
| WO | WO-2009/021924 | 2/2009 |
| WO | WO-2009/021924 A1 | 2/2009 |
| WO | WO-2009/124947 | 10/2009 |
| WO | WO-2009/124947 A1 | 10/2009 |

OTHER PUBLICATIONS

U.S. Appl. No. 12/967,337, Altwasser et al.
U.S. Appl. No. 13/021,242, Ewald et al.
U.S. Appl. No. 12/015,741, filed Jan. 17, 2008, Raichle, et al.
U.S. Appl. No. 12/039,231, filed Feb. 28, 2008, Cremer, et al.
U.S. Appl. No. 12/138,862, filed Jun. 13, 2008, Cremer, et al.
U.S. Appl. No. 12/138,823, filed Jun. 13, 2008, Raichle, et al.
U.S. Appl. No. 12/297,895, filed Oct. 21, 2008, Maurer, et al.
U.S. Appl. No. 12/298,453, filed Oct. 24, 2008, Lautensack, et al.
U.S. Appl. No. 12/301,352, filed Nov. 18, 2008, Mackewitz, et al.
U.S. Appl. No. 12/301,420, filed Nov. 18, 2008, Wilmer, et al.
U.S. Appl. No. 12/301,370, filed Nov. 18, 2008, Mackewitz, et al.
U.S. Appl. No. 12/305,698, filed Dec. 19, 2008, Wilmer, et al.
U.S. Appl. No. 12/520,648, filed Jun. 22, 2009, Wilmer, et al.

* cited by examiner

METHOD FOR STARTING A GAS-PHASE OXIDATION REACTOR

CROSS-REFERENCE TO RELATED APPLICATIONS

This application is a national stage application (under 35 U.S.C. §371) of PCT/EP2009/054168, filed Apr. 7, 2009 which claims benefit of European application 08154169.0, filed Apr. 7, 2008.

BACKGROUND OF THE INVENTION

The invention relates to the preparation of phthalic anhydride by gas phase oxidation of o-xylene. To this end, a gas stream which comprises molecular oxygen and o-xylene is generally passed through a multitude of tubes disposed in a reactor, in which a bed of at least one catalyst is present. To regulate the temperature, the tubes are surrounded by a heat carrier medium, for example a salt melt.

In spite of this thermostating, so-called "hotspots" form in the catalyst bed, at which the temperature is higher than in the remainder of the catalyst bed. These "hotspots" cause side reactions, such as the total combustion of the starting material, or lead to the formation of undesirable by-products which can be removed from the reaction product only with a high level of complexity, if at all, for example phthalide or benzoic acid.

To attenuate these hotspots, there has been a move in industry to arranging catalysts of different activity layer by layer in the catalyst bed, in which case the less active catalyst is generally arranged in the fixed bed such that the reaction gas mixture comes into contact with it first, i.e. it is present in the bed toward the gas inlet, whereas the more active catalyst is present toward the gas outlet from the catalyst bed (DE-A 25 46 268, EP 286 448, DE 29 48 163, EP 163 231).

To bring the reactor into operation, or to "start it up", the catalyst bed is typically brought by external heating to a temperature which is above the later operating temperature. As soon as the oxidation reaction commences, the reaction temperature is maintained by the marked exothermicity of the reaction and the external heating is reduced and finally switched off. However, the formation of a marked hotspot prevents a rapid startup phase, since, from a particular hotspot temperature, the catalyst can be damaged irreversibly. The loading of the gas stream with the hydrocarbon to be oxidized is therefore increased in small steps and has to be controlled very carefully.

WO 98/00778 discloses that the addition of temporary activity attenuators can lead to a shortening of the startup phase.

In spite of the proposed improvements mentioned above, long startup times of from 2 to 8 weeks or longer have been required to date. "Startup time" describes the time which is needed to bring the feed of the hydrocarbon to the desired end loading, i.e. to bring the oxidation to the steady state, without irreversibly damaging the catalyst. In this context, it should be ensured in particular that the hotspot does not exceed a certain critical value, since the selectivity and the lifetime of the catalyst are otherwise significantly impaired.

On the other hand, the salt bath temperature on startup cannot be selected at as low a level as desired, since increased contents of unconverted hydrocarbon and underoxidation products otherwise occur in the reaction product, which can lead to exceedance of emission and/or quality requirements. In the case of the industrially important oxidation of o-xylene to phthalic anhydride, the end loading is, for example, 80 g of o-xylene/m$^3$ (STP) of air or more. The catalysts based on vanadium oxide and titanium dioxide used to date are started up at temperatures of from 360 to 400° C. This ensures that the residual amount of o-xylene and the content of the phthalide underoxidation product are within the emission and quality requirements. In the course of the formation phase which then follows, the salt bath temperature is lowered (to typically about 350° C.) and the loading can be increased in parallel to target load.

WO 2005/063673 describes a process for preparing unsaturated aldehydes and/or carboxylic acids by partial oxidation over a fixed catalyst bed, wherein the reactor comprises a reaction zone in which unsaturated aldehydes are obtained as the main product, and a layer of inactive material is inserted within this reaction zone at the point at which the position of the hotspot is expected.

BRIEF SUMMARY OF THE INVENTION

It is an object of the invention to specify a process for starting up the gas phase oxidation reactor which combines a short startup time without exceedance of emission and/or quality requirements, long catalyst lifetime, high yield and low formation of by-products.

The object is achieved by a process for starting up a gas phase oxidation reactor for oxidation of o-xylene to phthalic anhydride, said reactor comprising at least one catalyst layer and being temperature-controllable by means of a heat carrier medium, wherein
a) the catalyst layer is interrupted by a moderator layer which is less catalytically active than the catalyst layer or is catalytically inactive,
b) a gas stream is passed through the reactor with an initial loading of o-xylene and at an initial temperature of the heat transfer medium,
c) the loading of the gas stream is increased to a target loading and, in parallel, the temperature of the heat transfer medium is lowered to an operating temperature.

A BRIEF DESCRIPTION OF THE FIGURES

DETAILED DESCRIPTION OF THE INVENTION

Figure 1:
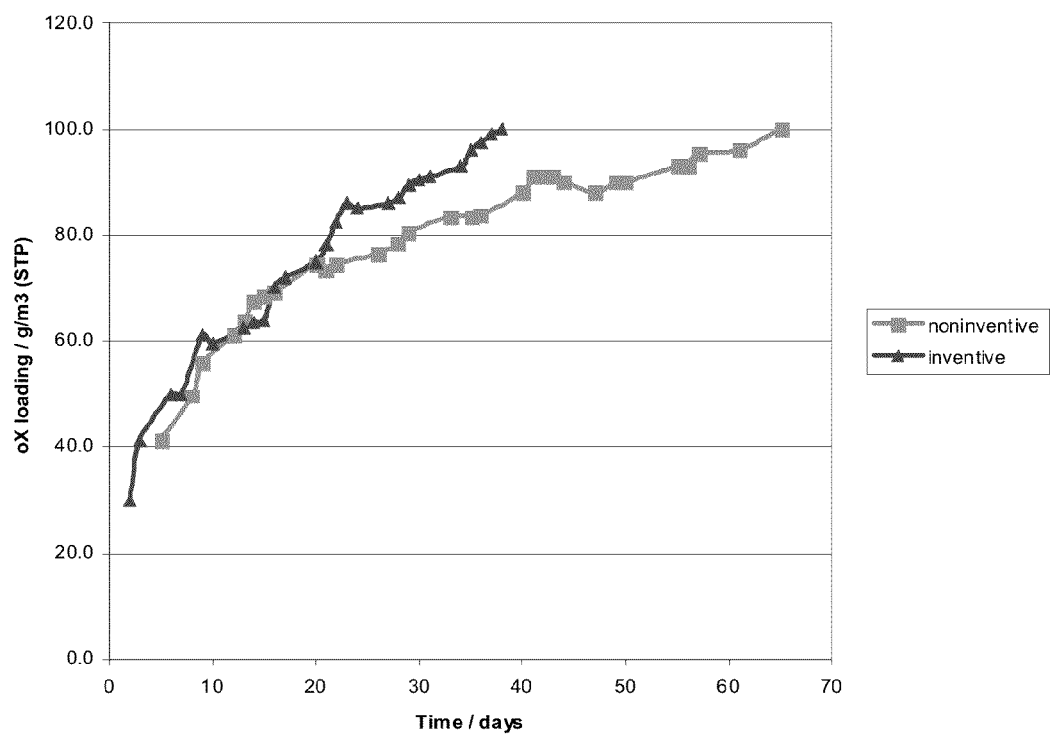
FIG. 1 shows the loading of the gas stream (g/m$^3$ (STP)) plotted against time (days) on startup of a reactor for oxidation of o-xylene to phthalic anhydride for a four-layer catalyst system whose first layer is interrupted by a moderator layer (inventive), and a corresponding catalyst system without moderator layer (noninventive).

The moderator layer is preferably disposed upstream of the position of an expected hotspot. "Upstream of the position of an expected hotspot" means that the predominant portion of the spatial extent of the moderator layer is upstream of the position of the hotspot. Preferably at least 60%, especially at least 80%, of the volume of the moderator layer is upstream of the position of an expected hotspot.

"Position of an expected hotspot" means the point in the reactor at which, in an identical catalyst bed under identical conditions, except that the catalyst layer is not interrupted by a moderator layer, the highest local temperature maximum (maximum hotspot) forms. When, for example, the process according to the invention is employed to start up a newly filled reactor, the position of the expected hotspot is generally known from earlier startup operations.

The exact position of the maximum hotspot depends on several parameters, more particularly the entrance temperature of the gas into the catalyst bed, the activity of the catalyst, the temperature of the heat transfer medium, the gas volume flow through the catalyst bed, the o-xylene loading, the pressure and any temperature inhomogeneities in the heat transfer medium. Since the position of the hotspot can therefore be forecast theoretically only with difficulty, it is appropriately determined by means of a comparative bed (without moderator layer), as detailed above.

The volume of the moderator layer is generally from 3 to 25%, preferably from 5 to 10%, of the volume of the catalyst layer which is interrupted by the moderator layer.

The reaction mixture which leaves the catalyst layer interrupted by the moderator layer comprises phthalic anhydride, phthalic anhydride underoxidation products and unconverted o-xylene. "Phthalic anhydride underoxidation products" are understood to mean $C_8$ species which have a lower oxidation state than phthalic anhydride and can be oxidized further to phthalic anhydride. They include in particular o-tolylaldehyde, o-toluic acid and phthalide. Phthalic anhydride makes up preferably more than 90 mol % of the sum of phthalic anhydride and phthalic anhydride underoxidation products.

In preferred embodiments, the reactor comprises at least two catalyst layers of different activity arranged in succession in flow direction of the gas stream, especially three, four or five catalyst layers. The successive catalyst layers differ in their activity.

Various configurations of the graduation of activity are possible. In a preferred embodiment, the activity of the catalysts increases constantly from one catalyst layer to the next in flow direction of the gas stream from the catalyst layer disposed closest to the gas inlet to the catalyst layer disposed closest to the gas outlet.

Activity of a catalyst or of a catalyst layer is understood to mean the conversion which is measured in a test system under identical conditions (especially with regard to catalyst volume, gas hourly space velocity (GHSV) and air rate, temperature of the heat carrier medium, hydrocarbon loading of the gaseous stream). The higher the conversion of a catalyst or of a catalyst layer, the higher its activity. This method is suitable especially for comparing activities or for determining relative catalyst activities.

If the reactor comprises more than one catalyst layer, the moderator layer preferably interrupts the catalyst layer furthest upstream, i.e. closest to the reactor inlet.

In general, the increase in the loading of the gas stream is regulated such that the temperature at the hotspot in the catalyst layer does not exceed a predefined limit, since, from a particular hotspot temperature, the catalyst can be damaged irreversibly, which impairs the selectivity and the lifetime of the catalyst. The hotspot temperature can be determined with reference to the temperature profile, which can be determined easily, for example, by means of thermocouples which are arranged in thermal tubes at different heights, for example equidistantly, or with a height-adjustable thermocouple.

In the case of catalysts whose catalytically active material comprises vanadium pentoxide and titanium dioxide, the hotspot temperature preferably does not exceed a value of 450° C.

The loading of the gas stream with o-xylene can be increased, for example, at a rate of from 0.5 to 10 $g/m^3$ (STP)·day.

In general, the initial loading is at least 30 $g/m^3$ (STP) lower than the target loading. The minimum loading of the gas stream is generally 30 g of o-xylene/$m^3$ (STP), because homogeneous spraying of the o-xylene metered in liquid form is ensured only from this amount.

The target loading is considered to be the loading of the gas stream with o-xylene in the steady state, i.e. after the startup phase has ended during productive operation in the reactor. The target loading is generally from 60 to 110 $g/m^3$ (STP), usually from 80 to 100 $g/m^3$ (STP).

In general, the initial temperature is at least 30° C. higher than the operating temperature, usually from 35 to 50° C. higher than the operating temperature. Operating temperature is considered to be the temperature of the heat carrier medium in the steady state, i.e. after the startup phase has ended during productive operation in the reactor. To compensate for declining catalyst activity, in the operating state, the temperature of the heat transfer medium can, however, be increased over a long period (less than 10° C./year).

In general, the operating temperature is from 340 to 365° C., preferably from 345 to 355° C.

The invention envisages a moderator layer which is arranged such that it is passed through by the gas stream which leaves the upstream catalyst bed before it enters the downstream catalyst bed.

The moderator layer provided in accordance with the invention brings about cooling of the gas stream before it enters the bed of the catalyst disposed downstream of the moderator layer. Owing to the cooling, in the part of the catalyst bed disposed downstream of the moderator layer, a less marked hotspot forms. Therefore, in the course of startup, it is possible to increase the loading of the gas stream with o-xylene more rapidly and thus to shorten the startup time.

The moderator layer consists appropriately of a bed of a particulate material. With regard to easy filling of the reactor and a homogeneous pressure drop, the particulate material typically has similar dimensions to the catalyst particles.

The moderator layer may be catalytically inactive. In this case, it consists of an inert material, as, for example, also used as catalyst support. Suitable support materials are, for example, quartz ($SiO_2$), porcelain, magnesium oxide, tin dioxide, silicon carbide, rutile, alumina ($Al_2O_3$), aluminum silicate, steatite (magnesium silicate), zirconium silicate, cerium silicate or mixtures of these support materials. The moderator layer may also comprise fabrics or knits of fibers or metal wires.

The moderator layer may also have catalytic activity. In this case, the moderator layer is less catalytically active than the catalyst bed which is interrupted by the moderator layer. This can be achieved by a high content of deactivating additives, low active composition content, dilution of a catalyst with inert material and/or other measures which are familiar to those skilled in the art.

At least in the catalyst layer which is interrupted by the moderator layer provided in accordance with the invention, and preferably in all catalyst layers, preferably at least catalysts whose catalytically active material comprises vanadium pentoxide ($V_2O_5$) and titanium dioxide (preferably in the anatase polymorph) are used. Measures for controlling the activity of gas phase oxidation catalysts based on vanadium pentoxide and titanium dioxide are known per se to those skilled in the art.

For instance, the catalytically active material may comprise compounds which, as promoters, influence the activity and selectivity of the catalyst.

Examples of activity- and selectivity-influencing factors include alkali metal compounds, especially cesium oxide, lithium oxide, potassium oxide, sodium oxide and rubidium oxide, and phosphorus or sulfur compounds.

A further means of controlling the activity consists in varying the proportion of the active material or of the $V_2O_5$ content in the total weight of the catalyst, higher active material or $V_2O_5$ contents causing a higher activity and vice versa.

The catalysts used in the process according to the invention are generally coated catalysts in which the catalytically active material is applied in coating form on an inert support. The layer thickness of the catalytically active material is generally from 0.02 to 0.2 mm, preferably from 0.05 to 0.15 mm. In general, the catalysts have an active material layer applied in coating form on an inert support.

The inert support materials used may be virtually all prior art support materials, as used advantageously in the preparation of coated catalysts for the oxidation of aromatic hydrocarbons to aldehydes, carboxylic acids and/or carboxylic anhydrides, for example quartz ($SiO_2$), porcelain, magnesium oxide, tin dioxide, silicon carbide, rutile, alumina ($Al_2O_3$), aluminum silicate, steatite (magnesium silicate), zirconium silicate, cerium silicate, or mixtures of these support materials. The support material is generally nonporous. Advantageous support materials which should be emphasized are in particular steatite and silicon carbide. The shape of the support material is generally not critical for the inventive precatalysts and coated catalysts. For example, catalyst supports in the form of spheres, rings, tablets, spirals, tubes, extrudates or spall may be used. The dimensions of these catalyst supports correspond to those catalyst supports typically used for the preparation of coated catalysts for the gas phase partial oxidation of aromatic hydrocarbons. Preference is given to using steatite in the form of spheres having a diameter of from 3 to 6 mm, or of rings having an external diameter of from 5 to 9 mm and a length of from 4 to 7 mm.

The individual layers of the coated catalyst can be applied by any methods known per se, for example by spray application of solutions or suspensions in a coating drum, or coating with a solution or suspension in a fluidized bed. It is possible to add organic binders, preferably copolymers, advantageously in the form of an aqueous dispersion, of vinyl acetate/vinyl laurate, vinyl acetate/acrylate, styrene/acrylate, vinyl acetate/maleate, vinyl acetate/ethylene and hydroxyethylcellulose, to the catalytically active material, it being advantageous to use amounts of binders of from 3 to 20% by weight, based on the solids content of the solution of the active material constituents. When the catalytically active material is applied to the support without organic binder, coating temperatures above 150° C. are advantageous. When the abovementioned binders are added, the useable coating temperatures, depending on the binder used, are between 50 and 200° C. The binders applied burn off within a short time after the introduction of the catalyst and startup of the reactor. The binder addition additionally has the advantage that the active material adheres sufficiently on the support, so that transport and introduction of the catalyst are facilitated.

In a preferred embodiment of the process according to the invention with three catalyst layers, the catalysts have the following composition (the first layer being the layer arranged furthest upstream in flow direction of the gas stream):

For the First Layer:
from 7 to 10% by weight of active material based on the overall catalyst, this active material comprising:
from 6 to 11% by weight of vanadium pentoxide
from 1.2 to 3% by weight of antimony trioxide
from 0.1 to 1% by weight of an alkali (calculated as alkali metal), especially cesium oxide, and, as the remainder to 100% by weight, titanium dioxide, preferably in anatase polymorph with a BET surface area of from 5 to 30 $m^2/g$ For the Second Layer:
from 7 to 12% by weight of active material based on the overall catalyst, this active material comprising:
from 5 to 13% by weight of vanadium pentoxide
from 0 to 3% by weight of antimony trioxide
from 0 to 0.4% by weight of an alkali (calculated as alkali metal), especially cesium oxide
from 0 to 0.4% by weight of phosphorus pentoxide (calculated as P), and, as the remainder to 100% by weight, titanium dioxide, preferably in anatase polymorph with a BET surface area of from 10 to 40 $m^2/g$ For the Third Layer:
from 8 to 12% by weight of active material based on the overall catalyst, this active material comprising:
from 5 to 30% by weight of vanadium pentoxide
from 0 to 3% by weight of antimony trioxide
from 0 to 0.3% by weight of an alkali (calculated as alkali metal), especially cesium oxide
from 0.05 to 0.4% by weight of phosphorus pentoxide (calculated as P), and, as the remainder to 100% by weight, titanium dioxide, preferably in anatase polymorph with a BET surface area of from 15 to 50 $m^2/g$.

The ratio of the volumes occupied by the first, second and third layer is preferably 100 to 200:40 to 100:40 to 100.

In a preferred embodiment of the process according to the invention with four catalyst layers, the catalysts have the following composition (the first layer being the layer arranged furthest upstream in flow direction of the gas stream):

For the First Layer:
from 7 to 10% by weight of active material based on the overall catalyst, this active material comprising:
from 6 to 11% by weight of vanadium pentoxide
from 1.2 to 3% by weight of antimony trioxide
from 0.1 to 1% by weight of an alkali (calculated as alkali metal), especially cesium oxide, and, as the remainder to 100% by weight, titanium dioxide, preferably in anatase polymorph with a BET surface area of from 5 to 30 $m^2/g$ For the Second Layer:
from 7 to 10% by weight of active material based on the overall catalyst, this active material comprising:
from 4 to 15% by weight of vanadium pentoxide
from 0 to 3% by weight of antimony trioxide
from 0.1 to 1% by weight of an alkali (calculated as alkali metal), especially cesium oxide
from 0 to 0.4% by weight of phosphorus pentoxide (calculated as P), and, as the remainder to 100% by weight, titanium dioxide, preferably in anatase polymorph with a BET surface area of from 10 to 35 $m^2/g$ For the Third Layer:
from 7 to 10% by weight of active material based on the overall catalyst, this active material comprising:
from 5 to 13% by weight of vanadium pentoxide
from 0 to 3% by weight of antimony trioxide from 0 to 0.4% by weight of an alkali (calculated as alkali metal), especially cesium oxide from 0 to 0.4% by weight of phosphorus pentoxide (calculated as P), and, as the remainder to 100% by weight, titanium dioxide, preferably in anatase polymorph with a BET surface area of from 15 to 40 $m^2/g$ For the Fourth Layer:

from 8 to 12% by weight of active material based on the overall catalyst, this active material comprising:

from 10 to 30% by weight of vanadium pentoxide from 0 to 3% by weight of antimony trioxide from 0.05 to 0.4% by weight of phosphorus pentoxide (calculated as P), and, as the remainder to 100% by weight, titanium dioxide, preferably in anatase polymorph with a BET surface area of from 15 to 50 $m^2/g$.

The ratio of the volumes occupied by the first, second, third and fourth layer is preferably 80 to 160:30 to 100:30 to 100:30 to 100.

If desired, a downstream finishing reactor can also be provided for phthalic anhydride preparation, as described, for example, in DE-A 198 07 018 or DE-A 20 05 969 A. The catalyst used is preferably an even more active catalyst compared to the catalyst of the last layer.

The catalysts are typically charged into reaction tubes which are thermostated externally to the reaction temperature, for example with a heat carrier medium, for example a salt melt. The gas stream is passed over the catalyst bed thus prepared at temperatures of generally from 300 to 450° C., preferably from 320 to 420° C. and more preferably from 340 to 400° C., and at an elevated pressure of generally from 0.1 to 2.5 bar, preferably from 0.3 to 1.5 bar, with a superficial velocity of generally from 750 to 5000 $h^{-1}$.

The reaction gas fed to the catalyst is generally obtained by mixing a gas which comprises molecular oxygen and, apart from oxygen, may also comprise suitable reaction moderators and/or diluents such as steam, carbon dioxide and/or nitrogen, with o-xylene. The molecular oxygen-comprising gas may comprise generally from 1 to 100 mol %, preferably from 2 to 50 mol % and more preferably from 10 to 30 mol % of oxygen, from 0 to 30 mol %, preferably from 0 to 10 mol % of steam, and from 0 to 50 mol %, preferably from 0 to 1 mol % of carbon dioxide, remainder nitrogen. Preference is given to using air.

It is possible for two or more zones, preferably two zones, of the catalyst bed present in the reaction tube to be thermostated to different reaction temperatures, for which, for example, reactors with separate salt baths can be used. Preference is given to performing the gas phase oxidation at one temperature of the heat carrier medium without division into temperature zones. Preference is given to conducting the heat carrier medium in countercurrent to the flow direction of the reaction gas in the reaction tubes. The temperature of the heat transfer medium is generally considered to be its temperature on entry into the reactor.

The invention is illustrated in detail by the appended drawings and the examples which follow.

COMPARATIVE EXAMPLE

The following catalysts 1 to 4 were used. The catalysts comprised shaped steatite bodies (magnesium silicate) in the form of rings (7×7×4 mm, ED×L×ID) with applied active material.

Catalyst 1: active material content: 8.0% of the total weight of the catalyst. Active material composition (after calcination at 400° C. for 4 h): 7.1% by weight of $V_2O_5$, 1.8% by weight of $Sb_2O_3$, 0.36% by weight of Cs.

Catalyst 2: active material content: 8.0% of the total weight of the catalyst. Active material composition (after calcination at 400° C. for 4 h): 7.1% by weight of $V_2O_5$, 2.4% by weight of $Sb_2O_3$, 0.26% by weight of Cs.

Catalyst 3: active material content: 8.0% of the total weight of the catalyst. Active material composition (after calcination at 400° C. for 4 h): 7.1% by weight of $V_2O_5$, 2.4% by weight of $Sb_2O_3$, 0.10% by weight of Cs.

Catalyst 4: active material content: 8.0% of the total weight of the catalyst. Active material composition (after calcination at 400° C. for 4 h): 20.0% by weight of $V_2O_5$, 0.38% by weight of P.

The reactor used was a reactor consisting of an iron tube with an internal width of 25 mm and a length of 360 cm. For temperature control, the iron tube was surrounded by a salt melt. Beginning with the catalyst 4, the above catalysts were introduced so as to give rise to the following bed length distribution: 130/50/70/70 cm (catalyst 1/catalyst 2/catalyst 3/catalyst 4).

The reactor also comprised a thermal tube which allowed temperature measurement axially along the catalyst beds. For this purpose, the thermal tube, in addition to the fixed catalyst bed, comprised a thermowell (external diameter 4 mm) which was charged only with a temperature sensor and was conducted along the center of the thermal tube.

Figure 3:
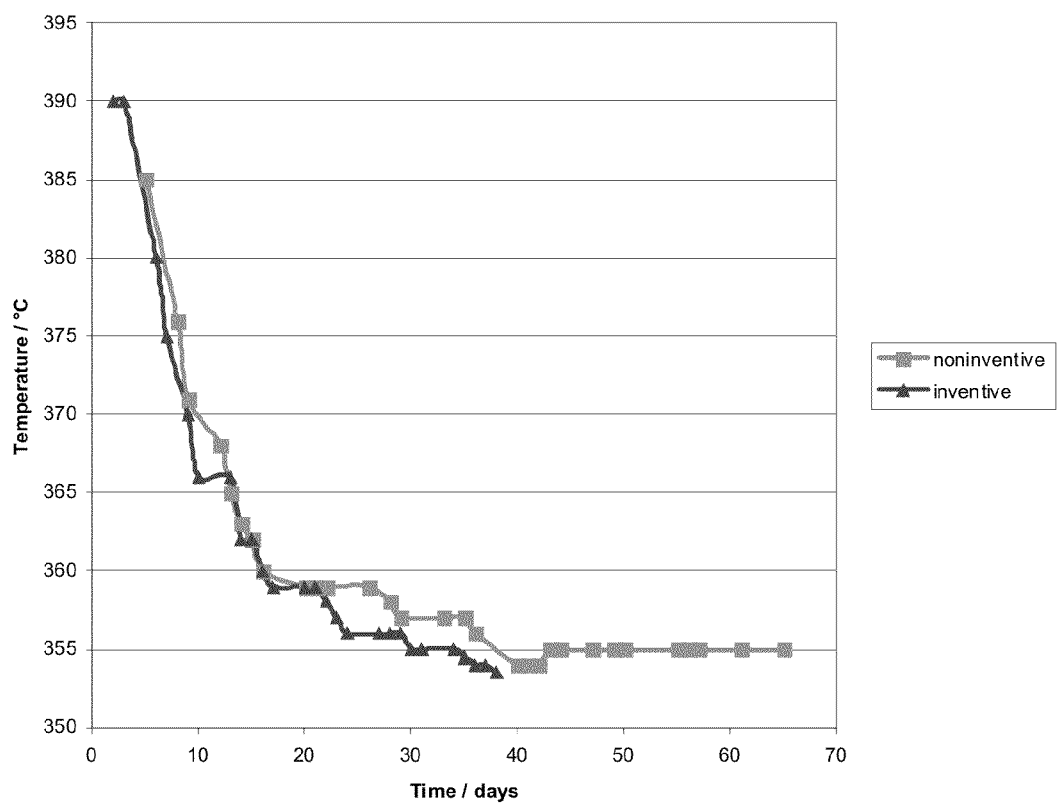
FIG. 3 shows the salt bath temperature plotted against time on startup of a reactor for oxidation of o-xylene to phthalic anhydride for a four-layer catalyst system whose first layer is interrupted by a moderator layer (inventive), and a corresponding catalyst system without moderator layer (noninventive).

To operate the system, an air/o-xylene mixture was passed through the main reactor from the top downward at a salt bath temperature of about 350° C. The loading of the air stream with o-xylene was increased from 30 $g/m^3$ (STP) to 100 $g/m^3$ (STP) over the course of 60 days, as shown by the square symbols in FIG. 1. At the same time, the salt bath temperature was lowered from 390° C. to 355° C., as shown by the square symbols in FIG. 3.

INVENTIVE EXAMPLE

The comparative example was repeated, except that, after 60 cm of the layer of catalyst 1, a 10 cm catalytically inactive layer of steatite rings (external diameter 7 mm, height 4 mm, internal diameter 4 mm, with two notches on the end faces) was introduced as a moderator layer. This gave rise to the following bed length distribution: 60/10/60/50/70/70 cm (catalyst 1a/moderator layer/catalyst 1b/catalyst 2/catalyst 3/catalyst 4).

The loading of the air stream with o-xylene was increased from 30 $g/m^3$ (STP) to 100 $g/m^3$ (STP) over the course of 40 days, as shown by the triangular symbols in FIG. 1. At the same time, the salt bath temperature was lowered from 390° C. to 353° C., as shown by the triangular symbols in FIG. 3.

Figure 2:
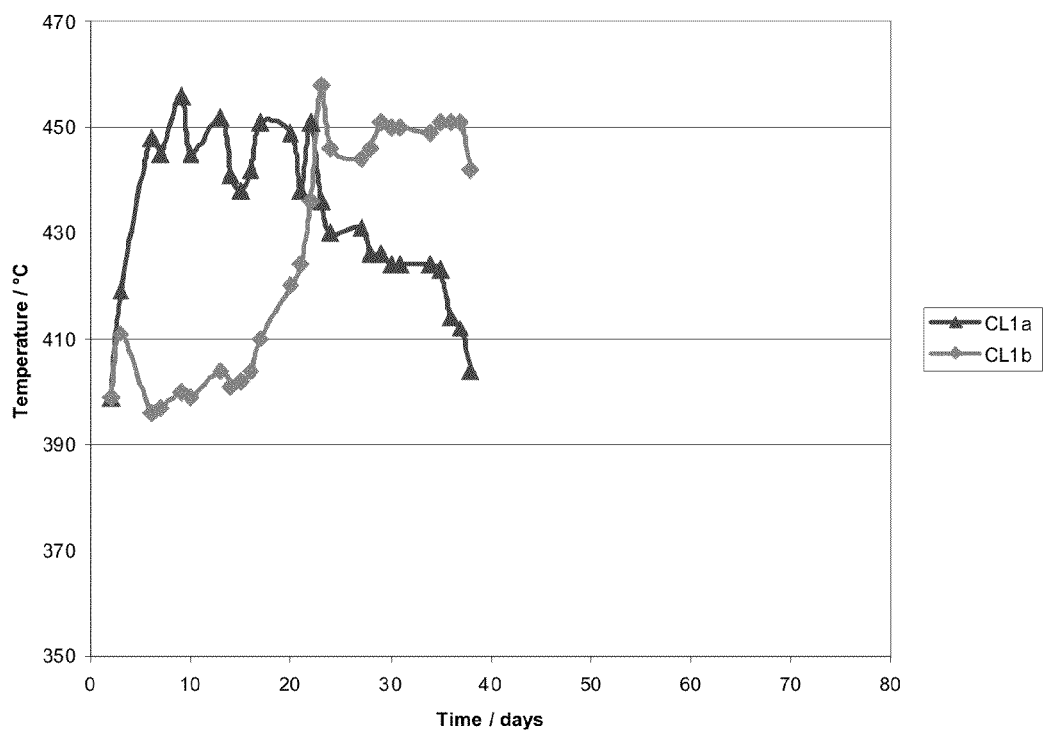
FIG. 2 shows the hotspot temperatures plotted against time in a bed of a catalyst 1 (CL 1a) disposed upstream of a moderator layer and of a bed of catalyst 1 (CL 1b) disposed downstream of the moderator layer.

FIG. 2 shows the plot of the hotspot temperature in the bed of catalyst 1 disposed upstream of the moderator layer (CL1a) and of the bed of catalyst 1 disposed downstream of the moderator layer (CL1b). At first, a hotspot forms in the region of bed CL1a disposed toward the reactor inlet. For as long as the hotspot is present in bed CL1a, the catalyst can be loaded no more rapidly than in the comparative example. With further lowering of the salt bath temperature (FIG. 3), the reaction starts up at an increasingly late stage and the hotspot shifts further downstream in the catalyst bed. The hotspot is shifted from the bed of catalyst 1 disposed upstream of the moderator layer (CL1a) to the bed of catalyst 1 disposed downstream of the moderator layer (CL1b). The intermediate cooling allows the loading to be increased very much more rapidly. The target loading is achieved as early as after about 40 days, while it is 60 days in the comparative example (square symbols).

The invention claimed is:

1. A process for starting up a gas phase oxidation reactor for oxidation of o-xylene to phthalic anhydride, said reactor comprising at least one catalyst layer and being temperature-controllable by means of a heat carrier medium, the catalyst layer comprising a catalyst whose catalytically active material comprises vanadium pentoxide and titanium dioxide, wherein
   a) the catalyst layer is interrupted by a moderator layer which is less catalytically active than the catalyst layer or is catalytically inactive,
   b) a gas stream is passed through the reactor with an initial loading of o-xylene and at an initial temperature of the heat transfer medium,
   c) the loading of the gas stream is increased to a target loading and, in parallel, the temperature of the heat transfer medium is lowered to an operating temperature wherein the reactor comprises at least two catalyst layers of different activity arranged in succession in flow direction of the gas stream and the moderator interrupts the catalyst layer further upstream.

2. The process according to claim 1, wherein the moderator layer is disposed upstream of the position of an expected hotspot.

3. The process according to claim 1, wherein the volume of the moderator layer is from 3 to 25% of the volume of the catalyst layer which is interrupted by the moderator layer.

4. The process according to claim 1, wherein the increase in the loading of the gas stream is regulated such that the temperature at the hotspot in the catalyst layer does not exceed 450° C.

5. The process according to claim 1, wherein the initial loading is at least 30 g/m$^3$ (STP) lower than the target loading.

6. The process according to claim 1, wherein the initial temperature is at least 30° C. higher than the operating temperature.

7. The process according to claim 1, wherein the target loading is from 60 to 10 g/m$^3$ (STP).

8. The process according to claim 1, wherein the operating temperature is from 340 to 365° C.

9. The process according to claim 1, wherein the loading is increased at a rate of from 0.5 to 10 g/m$^3$ (STP)·day.

* * * * *